(12) United States Patent
Burd et al.

(10) Patent No.: US 6,958,039 B2
(45) Date of Patent: Oct. 25, 2005

(54) METHOD AND INSTRUMENTS FOR NON-INVASIVE ANALYTE MEASUREMENT

(75) Inventors: John F. Burd, San Diego, CA (US); Gary Krantz, Laguna Beach, CA (US); William Sell, Petaluma, CA (US)

(73) Assignee: Oculir, Inc., San Diego, CA (US)

( * ) Notice: Subject to any disclaimer, the term of this patent is extended or adjusted under 35 U.S.C. 154(b) by 0 days.

(21) Appl. No.: 10/824,254

(22) Filed: Apr. 14, 2004

(65) Prior Publication Data

US 2004/0220458 A1    Nov. 4, 2004

Related U.S. Application Data

(60) Provisional application No. 60/467,355, filed on May 2, 2003.

(51) Int. Cl.[7] ................................................ A61B 5/00
(52) U.S. Cl. ........................ 600/309; 600/365; 600/473
(58) Field of Search ................................ 600/309, 365, 600/473

(56) References Cited

U.S. PATENT DOCUMENTS

| | | |
|---|---|---|
| 3,868,219 A | 2/1975 | Hurenkamp |
| 3,920,969 A | 11/1975 | Berglas |
| 3,958,560 A | 5/1976 | March |
| 4,014,321 A | 3/1977 | March |
| 4,055,175 A | 10/1977 | Clemens et al. |
| 4,151,845 A | 5/1979 | Clemens |
| 4,163,780 A | 8/1979 | Ishida et al. |
| 4,230,697 A | 10/1980 | Nishida et al. |
| 4,312,979 A | 1/1982 | Takemoto et al. |
| 4,313,934 A | 2/1982 | Kitamura et al. |
| 4,313,935 A | 2/1982 | Komori et al. |
| 4,330,533 A | 5/1982 | Takayama et al. |
| 4,390,622 A | 6/1983 | Cartwright |
| 4,396,763 A | 8/1983 | Tsuchiya et al. |
| 4,473,530 A | 9/1984 | Villa-Real |
| 4,482,543 A | 11/1984 | Suzuki et al. |
| 4,533,548 A | 8/1985 | Umezawa et al. |
| 4,557,933 A | 12/1985 | Haneishi et al. |
| 4,575,551 A | 3/1986 | Fujiyama et al. |
| 4,627,445 A | 12/1986 | Garcia et al. |
| 4,637,403 A | 1/1987 | Garcia et al. |

(Continued)

FOREIGN PATENT DOCUMENTS

| | | |
|---|---|---|
| CA | 1277617 | 12/1990 |

(Continued)

OTHER PUBLICATIONS

Cameron, et al., "The use of polarized laser light through the eye for noninvasive glucose monitoring", Diabetes Technology & Therapeutics, vol. 1, No. 2, 135-143 (1999).

(Continued)

*Primary Examiner*—Eric F. Winakur
*Assistant Examiner*—Matthew Kremer
(74) *Attorney, Agent, or Firm*—Stephen C. Beuerle; Procopio Cory Hargreaves & Savitch LLP

(57) ABSTRACT

The present invention is related to optical non-invasive methods and instruments to detect the level of analyte concentrations in the tissue of a subject. The spectra of mid-infrared radiation emitted from a subject's body are altered corresponding to the concentration of various compounds within the radiating tissue. In one aspect of the invention, an instrument measures the level of mid-infrared radiation from the subject's body surface, such as the eye, and determines a specific analyte's concentration based on said analyte's distinctive mid-infrared radiation signature.

7 Claims, 4 Drawing Sheets

U.S. PATENT DOCUMENTS

| | | | |
|---|---|---|---|
| 4,787,398 A | 11/1988 | Garcia et al. |
| 4,790,324 A | 12/1988 | O'Hara et al. |
| 4,797,840 A | 1/1989 | Fraden |
| 4,801,582 A | 1/1989 | Hikino et al. |
| 4,882,492 A | 11/1989 | Schlager |
| 4,898,813 A | 2/1990 | Albarella et al. |
| 4,901,728 A | 2/1990 | Hutchison |
| 4,901,729 A | 2/1990 | Saitoh et al. |
| 4,918,054 A | 4/1990 | Haneishi et al. |
| 4,932,789 A | 6/1990 | Egawa et al. |
| 4,975,367 A | 12/1990 | Albarella et al. |
| 5,009,230 A | 4/1991 | Hutchinson |
| 5,013,550 A | 5/1991 | Haneishi et al. |
| 5,024,533 A | 6/1991 | Egawa et al. |
| 5,054,487 A | 10/1991 | Clarke |
| 5,068,536 A | 11/1991 | Rosenthal |
| 5,070,874 A | 12/1991 | Barnes et al. |
| 5,077,476 A | 12/1991 | Rosenthal |
| 5,086,229 A | 2/1992 | Rosenthal et al. |
| 5,137,023 A | 8/1992 | Mendelson et al. |
| 5,167,235 A | 12/1992 | Seacord et al. |
| 5,167,265 A | 12/1992 | Sakamoto |
| 5,169,235 A | 12/1992 | Tominaga et al. |
| 5,178,464 A | 1/1993 | Fraden |
| 5,194,615 A | 3/1993 | Jensen |
| 5,209,231 A | 5/1993 | Cote et al. |
| 5,212,066 A | 5/1993 | Albarella et al. |
| 5,222,496 A | 6/1993 | Clarke et al. |
| 5,243,983 A | 9/1993 | Tarr et al. |
| 5,267,152 A | 11/1993 | Yang et al. |
| 5,279,294 A | 1/1994 | Anderson et al. |
| 5,313,941 A | 5/1994 | Braig et al. |
| 5,321,265 A | 6/1994 | Block |
| 5,332,667 A | 7/1994 | Kado et al. |
| 5,352,411 A | 10/1994 | Khuri |
| 5,361,758 A | 11/1994 | Hall et al. |
| 5,370,114 A | 12/1994 | Wong et al. |
| 5,424,201 A | 6/1995 | Kado et al. |
| 5,424,545 A | 6/1995 | Block et al. |
| 5,433,197 A | 7/1995 | Stark |
| 5,434,412 A | 7/1995 | Sodickson et al. |
| 5,448,992 A | 9/1995 | Kupershmidt |
| 5,459,317 A | 10/1995 | Small et al. |
| 5,476,656 A | 12/1995 | Kawaguchi et al. |
| 5,484,715 A | 1/1996 | Kado et al. |
| 5,497,772 A | 3/1996 | Schulman et al. |
| 5,515,847 A | 5/1996 | Braig et al. |
| 5,535,743 A | 7/1996 | Backhaus et al. |
| 5,553,613 A | 9/1996 | Parker |
| 5,553,616 A | 9/1996 | Ham et al. |
| 5,556,761 A | 9/1996 | Phillips |
| 5,565,342 A | 10/1996 | Yoneta et al. |
| 5,615,672 A | 4/1997 | Braig et al. |
| 5,660,163 A | 8/1997 | Schulman et al. |
| 5,666,956 A | 9/1997 | Buchert |
| 5,687,721 A | 11/1997 | Kuhls |
| 5,713,353 A | 2/1998 | Castano |
| 5,719,034 A | 2/1998 | Kiser et al. |
| 5,755,231 A | 5/1998 | Krantz et al. |
| 5,756,318 A | 5/1998 | Kosuna |
| 5,786,584 A | 7/1998 | Button et al. |
| 5,788,632 A | 8/1998 | Pezzaniti et al. |
| 5,791,344 A | 8/1998 | Schulman et al. |
| 5,820,557 A | 10/1998 | Hattori et al. |
| 5,823,966 A | 10/1998 | Buchert |
| 5,835,215 A | 11/1998 | Toida et al. |
| 5,896,198 A | 4/1999 | Chou et al. |
| 5,910,109 A | 6/1999 | Peters et al. |
| 5,961,449 A | 10/1999 | Toida et al. |
| 5,969,815 A | 10/1999 | Toida et al. |
| 5,991,653 A | 11/1999 | Richards-Kortum et al. |
| 5,995,236 A | 11/1999 | Roth et al. |
| 5,995,860 A | 11/1999 | Sun et al. |
| 6,025,597 A | 2/2000 | Sterling et al. |
| 6,026,314 A | 2/2000 | Amerov et al. |
| 6,049,727 A | 4/2000 | Crothall |
| 6,061,582 A | 5/2000 | Small et al. |
| 6,072,180 A | 6/2000 | Kramer et al. |
| 6,088,605 A | 7/2000 | Griffith et al. |
| 6,113,537 A | 9/2000 | Castano |
| 6,122,536 A | 9/2000 | Sun et al. |
| 6,162,397 A | 12/2000 | Jurik et al. |
| 6,181,957 B1 | 1/2001 | Lambert et al. |
| 6,203,496 B1 | 3/2001 | Gael et al. |
| 6,246,893 B1 | 6/2001 | Gobeli |
| 6,268,604 B1 | 7/2001 | Boyadzhyan-Sevak |
| 6,362,144 B1 | 3/2002 | Berman et al. |
| 6,418,332 B1 | 7/2002 | Mastrototaro et al. |
| 6,421,548 B1 | 7/2002 | Berman et al. |
| 6,424,848 B1 | 7/2002 | Berman et al. |
| 6,424,849 B1 | 7/2002 | Berman et al. |
| 6,424,850 B1 | 7/2002 | Lambert et al. |
| 6,424,851 B1 | 7/2002 | Berman et al. |
| 6,430,424 B1 | 8/2002 | Berman et al. |
| 6,441,388 B1 | 8/2002 | Thomas et al. |
| 6,442,410 B1 | 8/2002 | Steffes |
| 6,445,938 B1 | 9/2002 | Berman et al. |
| 2001/0031914 A1 | 10/2001 | Gobeli et al. |
| 2001/0034478 A1 * | 10/2001 | Lambert et al. ............ 600/318 |
| 2002/0007113 A1 | 1/2002 | March et al. |
| 2002/0016535 A1 | 2/2002 | Martin et al. |
| 2002/0031840 A1 | 3/2002 | Albarella et al. |
| 2002/0038080 A1 | 3/2002 | Makarewicz et al. |
| 2002/0049389 A1 * | 4/2002 | Abreu ........................ 600/318 |
| 2002/0123677 A1 | 9/2002 | Miki et al. |
| 2003/0018271 A1 | 1/2003 | Kimble |

FOREIGN PATENT DOCUMENTS

| | | |
|---|---|---|
| CA | 2056868 | 6/1993 |
| DE | 42 00 332 A1 | 7/1993 |
| DE | 195 38 372 A1 | 4/1997 |
| DE | 198 07 939 C1 | 9/1999 |
| EP | 0 160 768 A1 | 11/1985 |
| EP | 0 181 578 B1 | 5/1986 |
| EP | 0 199 484 B1 | 10/1986 |
| EP | 0 201 332 B1 | 11/1986 |
| EP | 0 212 501 B1 | 3/1987 |
| EP | 0 239 926 B1 | 10/1987 |
| EP | 0 240 849 B1 | 10/1987 |
| EP | 0 326 029 B1 | 8/1989 |
| EP | 0 331 821 A1 | 9/1989 |
| EP | 0 426 358 A1 | 5/1991 |
| EP | 0 449 525 A1 | 10/1991 |
| EP | 0 165 973 B1 | 3/1992 |
| EP | 0 538 050 B1 | 4/1993 |
| EP | 0 335 884 B1 | 5/1993 |
| EP | 0 548 418 A1 | 6/1993 |
| EP | 0 317 121 B1 | 2/1994 |
| EP | 0 290 610 B1 | 8/1994 |
| EP | 0 536 187 B1 | 9/1994 |
| EP | 0 304 304 B1 | 11/1994 |
| EP | 0 478 550 B1 | 1/1995 |
| EP | 0 382 120 B1 | 5/1995 |
| EP | 0 382 121 B1 | 8/1995 |
| EP | 0 459 367 B1 | 1/1996 |
| EP | 0 561 872 B1 | 8/1996 |
| EP | 0 536 304 B1 | 12/1996 |
| EP | 0 589 191 B1 | 3/1997 |
| EP | 0 762 311 A2 | 3/1997 |
| EP | 0 657 028 B1 | 7/1997 |
| EP | 0 618 232 B1 | 12/1997 |
| EP | 0 456 716 B1 | 3/1998 |
| EP | 0 404 562 B1 | 8/1998 |

| | | |
|---|---|---|
| EP | 0 721 579 B1 | 3/2000 |
| EP | 0 985 930 A2 | 3/2000 |
| EP | 0 650 591 B1 | 4/2000 |
| EP | 0 670 492 B1 | 5/2001 |
| EP | 0 826 777 B1 | 8/2001 |
| EP | 0 828 533 B1 | 8/2001 |
| EP | 1 130 395 A2 | 9/2001 |
| EP | 0 714 024 B1 | 1/2002 |
| EP | 0 682 494 B1 | 4/2002 |
| EP | 0 733 647 B1 | 5/2002 |
| EP | 0 807 812 B1 | 5/2002 |
| EP | 0 630 203 B1 | 7/2002 |
| EP | 1 219 232 A1 | 7/2002 |
| JP | 04-339257 | 11/1992 |
| JP | 07-070209 | 3/1995 |
| JP | 08-037987 | 2/1996 |
| JP | 09-028671 | 2/1997 |
| JP | 09-215679 | 8/1997 |
| JP | 09-234190 | 9/1997 |
| JP | 09-299333 | 11/1997 |
| JP | 10-142225 | 5/1998 |
| JP | 11-070101 | 3/1999 |
| JP | 11-137538 | 5/1999 |
| JP | 11-188009 | 7/1999 |
| JP | 11-216131 | 8/1999 |
| JP | 11-239567 | 9/1999 |
| JP | 11-244243 | 9/1999 |
| JP | 2000-074829 | 3/2000 |
| JP | 2000-074915 | 3/2000 |
| JP | 2000-189404 | 7/2000 |
| JP | 2000-258344 | 9/2000 |
| JP | 2001-037741 | 2/2001 |
| JP | 2001-041955 | 2/2001 |
| JP | 2001-174405 | 6/2001 |
| JP | 2002-202258 | 7/2002 |
| WO | WO 88/04328 | 6/1988 |
| WO | WO 90/07905 | 7/1990 |
| WO | WO 92/07511 | 5/1992 |
| WO | WO 93/00856 | 1/1993 |
| WO | WO 93/09711 | 5/1993 |
| WO | WO 95/05599 | 2/1995 |
| WO | WO 95/22046 | 8/1995 |
| WO | WO 97/01986 | 1/1997 |
| WO | WO 97/13448 | 4/1997 |
| WO | WO 97/25915 | 7/1997 |
| WO | WO 97/28438 | 8/1997 |
| WO | WO 97/39686 | 10/1997 |
| WO | WO 97/43947 | 11/1997 |
| WO | WO 98/00703 | 1/1998 |
| WO | WO 98/01071 | 1/1998 |
| WO | WO 98/52469 | 11/1998 |
| WO | WO 99/18848 | 4/1999 |
| WO | WO 99/43255 | 9/1999 |
| WO | WO 99/44496 | 9/1999 |
| WO | WO 00/02479 | 1/2000 |
| WO | WO 00/21437 | 4/2000 |
| WO | WO 00/60350 | 10/2000 |
| WO | WO 01/10294 A1 | 2/2001 |
| WO | WO 01/22871 A1 | 4/2001 |
| WO | WO 01/45560 A1 | 6/2001 |
| WO | WO 01/79818 A2 | 10/2001 |
| WO | WO 02/16905 A2 | 2/2002 |
| WO | WO 02/060321 A2 | 8/2002 |
| WO | WO 02/065090 A2 | 8/2002 |
| WO | WO 00/16692 | 3/2003 |

OTHER PUBLICATIONS

Cameron, et al., "Measurement of the glucose transport time delay between the blood and aqueous humor of the eye for the eventual development of a noninvasive glucose sensor", Diabetes Technology & Therapeutics, vol. 3, No. 2, 201-207 (2001).

Steffes, "Laser-based measurement of glucose in the ocular aqueous humor: An efficacious portal for determination of serum glucose levels", Diabetes Technology & Therapeutics, vol. 1, No. 2, 129-133 (1999).

* cited by examiner

1000 mg/dl Glucose in Water

METHOD AND INSTRUMENTS FOR NON-INVASIVE ANALYTE MEASUREMENT

CROSS-REFERENCE TO RELATED APPLICATION

Applicants claim the benefit of prior provisional application 60/467,355, filed on May 2, 2003 under 35 U.S.C. 119(e).

FIELD OF THE INVENTION

The present invention is related to optical non-invasive methods and instruments to detect the presence or measure the concentration of a wide range of analytes, such as glucose, in the tissue of a subject. The spectra of mid-infrared radiation emitted from the subject's body are altered corresponding to the presence, absence or concentration of the analyte within the subject's tissue. In one aspect of the invention, an instrument measures the level of mid-infrared radiation from a surface of the subject's body, including but not limited to mid-infrared radiation emitted from any body surface, such as the skin or the eye, any orifice, piercing tract, or cavity, such as the mouth, ear or nose, and determines a specific analyte's presence or concentration based on said analyte's distinctive mid-infrared radiation signature. The measurements made by the instrument of the present invention do not require direct contact of the instrument with a surface of a subject's body.

BACKGROUND OF THE INVENTION

Diabetes remains one of the most serious and undertreated diseases facing the worldwide healthcare system. Diabetes is a chronic disease where the body fails to maintain normal levels of glucose in the bloodstream. It is now the fifth leading cause of death from disease in the U.S. today and accounts for about 15% of the entire healthcare budget. People with diabetes are classified into two groups: Type 1 (formerly known as "juvenile onset" or "insulin dependent" diabetes, that are required to take insulin to maintain life) and Type 2 (formerly known as "adult onset" or "non-insulin dependent," that may require insulin but may sometimes be treated by diet and oral hypoglycemic drugs). In both cases, without dedicated and regular blood glucose measurement, all patients face the possibility of the complications of diabetes that include cardiovascular disease, kidney failure, blindness, amputation of limbs and premature death.

The number of cases of diabetes in the U.S. has jumped 40% in the last decade. This high rate of growth is believed to be due to a combination of genetic and lifestyle origins that appear to be a long-term trend, including obesity and poor diet. The American Diabetes Association (ADA) and others estimate that about 17 million Americans and over 150 million people worldwide have diabetes, and it is estimated that up to 40% of these people are currently undiagnosed. American Diabetes Association, "Facts & Figures."

Diabetes must be "controlled" in order to delay the onset of the disease complications. Therefore, it is essential for people with diabetes to measure their blood glucose levels several times per day in an attempt to keep their glucose levels within the normal range (80 to 130 mg/dL). These glucose measurements are used to determine the amount of insulin or alternative treatments necessary to bring the glucose level to within target limits. Self-Monitoring of Blood Glucose (SMBG) is an ongoing process repeated multiple times per day for the rest of the patient's lifetime.

All currently FDA approved invasive or "less-invasive" (blood taken from the arm or other non-fingertip site) glucose monitoring products currently on the market require the drawing of blood in order to make a quantitative measurement of blood glucose. The ongoing and frequent measurement requirements (1 to possibly 10 times per day) presents all diabetic patients with pain, skin trauma, inconvenience, and infection risk resulting in a general reluctance to frequently perform the critical measurements necessary for selecting the appropriate insulin dose or other therapy.

These current product drawbacks have led to a poor rate of patient compliance. Among Type 1 diabetics, 39% measure their glucose levels less than once per day and 21% do not monitor their glucose at all. Among Type 2 diabetics who take insulin, only 26% monitor at least once per day and 47% do not monitor at all. Over 75% of non-insulin-taking Type 2 diabetics never monitor their glucose levels. Roper Starch Worldwide Survey. Of 1,186 diabetics surveyed, 91% showed interest in a non-invasive glucose monitor. [www.childrenwithdiabetes.com] As such, there is both a tremendous interest and clinical need for a non-invasive glucose sensor.

The present invention seeks to replace the currently used blood glucose measurement methods, devices and instruments, including invasive measures and the use of glucose test strips, with an optical non-invasive instrument.

Various methods have been developed related to non-invasive glucose sensing using a dermal testing site such as the finger or earlobe. These methods primarily employ instruments which measure blood-glucose concentration by generating and measuring light only in the near-infrared radiation spectrum. For example, U.S. Pat. No. 4,882,492 (the '492 patent), expressly incorporated by reference herein, is directed to an instrument which transmits near-infrared radiation through a sample to be tested on the skin surface of a human. In the '492 patent, the near-infrared radiation that passes through the sample is split into two beams, wherein one beam is directed through a negative correlation filter and the second through a neutral density filter. The differential light intensity measured through the filters of the two light beams is proportional to glucose concentration according to the '492 patent.

U.S. Pat. No. 5,086,229 (the '229 patent), expressly incorporated by reference herein, is directed to an instrument which generates near-infrared radiation within the spectrum of about 600 to about 1100 nanometers. According to the '229 patent, a person places their finger in between the generated near-infrared radiation source and a detector, which correlates the blood-glucose concentration based on the detected near-infrared radiation. Similarly, U.S. Pat. No. 5,321,265 (the '265 patent), expressly incorporated by reference herein, also measures blood-glucose level using both near-infrared radiation and the fingertip as a testing site. The detectors disclosed in the '265 patent further comprise silicon photocells and broad bandpass filters.

U.S. Pat. No. 5,361,758 (the '758 patent), expressly incorporated by reference herein, is directed to an instrument which measures near-infrared radiation that is either transmitted through or is reflected from the finger or earlobe of a human. In the '758 patent, the transmitted or reflected light is separated by a grating or prism, and the near-infrared radiation is detected and correlated with blood-glucose concentration. This instrument of the '758 patent also comprises an additional timing and control program wherein the device takes measurements specifically in between heartbeats and can also adjust for temperature.

U.S. Pat. No. 5,910,109 (the '109 patent), expressly incorporated by reference herein, is also directed to an instrument for measuring blood-glucose concentration using near-infrared radiation and the earlobe as the testing site. The instrument of the '109 patent comprises four light sources of a very specific near-infrared emission spectrum, and four detectors having specific near-infrared detection spectra corresponding to the wavelength of the light sources. The signals detected by the four distinct detectors are averaged, and these averages are analyzed to determine blood-glucose concentration according to the '109 patent.

The technique of using near-infrared radiation, wherein the near-infrared radiation is transmitted through or reflected from a dermal testing site and monitored for measuring glucose in vivo, is known to be inaccurate. The glucose concentration of interest is in the blood or the interstitial fluid, not on the surface of the dermis. Therefore these methods must penetrate down into the layers beneath the top layers of dermis. There are a number of substances in the dermis that can interfere with the near-infrared glucose signal. Additionally, there is a wide variation in the human dermis, both between individuals and within a given individual. Moreover, glucose simply lacks a satisfactory distinguishable "fingerprint" in the near-infrared radiation spectrum. Because near-infrared radiation is not sufficiently adsorbed by glucose and because of the level of tissue interferences found in the dermis, this technique is substantially less desirable for the accurate measurement of blood-glucose concentrations.

U.S. Pat. No. 6,362,144 (the '144 patent), expressly incorporated by reference herein, discloses using the fingertip as a testing site, however, the described instrument uses attenuated total reflection (ATR) infrared spectroscopy. According to the '144 patent, a selected skin surface, preferably the finger, is contacted with an ATR plate while ideally maintaining the pressure of contact. In the '144 patent, the skin is then irradiated with a mid-infrared beam, wherein said infrared radiation is detected and quantified to measure blood-glucose levels. This technique is not ideal, however, if the surface of tissue from which the measurement is taken is very dense in the wavelength region of interest or is not amenable to direct contact with the ATR plate, such as an eye, nose, mouth, or other orifice, cavity or piercing tract.

The minimal depth of peripheral capillaries in epithelial tissues is typically about 40 microns. Again, there are physical characteristics as well as a number of substances present in the skin that can interfere with the desired glucose-specific signal. While useful in the laboratory, both the near-infrared transmission methods, and the ATR method mentioned above are not practical, or may not be adequate for use in monitoring blood glucose concentration in patients.

Methods have also been developed related to non-invasive glucose sensing using the eye as a testing site. For example, in both U.S. Pat. Nos. 3,958,560 (the '560 patent) and 4,014,321 (the '321 patent), both expressly incorporated by reference herein, a device utilizing the optical rotation of polarized light is described. In the '560 and the '321 patents, the light source and light detector are incorporated into a contact lens which is placed on the surface of the eye whereby the eye is scanned using a dual source of polarized radiation, each source transmitting in a different absorption spectrum at one side of the cornea or aqueous humor. The optical rotation of the radiation that passes through the cornea correlates with the glucose concentration in the cornea according to the '560 and '321 patents. While this method would be termed, "non-invasive," because the withdrawal of blood is not required, it may still cause significant discomfort or distort vision of the user because of the need to place the sensor directly on the eye.

U.S. Pat. No. 5,009,230 (the '230 patent), expressly incorporated by reference herein, uses a polarized light beam of near-infrared radiation within the range of 940 to 1000 nm. In the '230 patent, the amount of rotation imparted by glucose present in the bloodstream of the eye on the polarized light beam is measured to determine glucose concentration. Again, the accuracy is limited because glucose simply lacks a sufficiently distinguishable "fingerprint" in this near-infrared radiation spectrum.

Both U.S. Pat. No. 5,209,231 (the '231 patent), and International Publication No. WO 92/07511 (the '511 application), both expressly incorporated by reference herein, similarly disclose the use of polarized light, which is initially split by a beam splitter into a reference beam and a detector beam, and then transmitted through a specimen, preferably the aqueous humor of the eye. The amount of phase shift as compared between the transmitted reference and detector beams are correlated to determine glucose concentration in the '231 patent and '511 application. U.S. Pat. No. 5,535,743 (the '743 patent), expressly incorporated by reference herein, measures diffusely reflected light provided by the surface of the iris as opposed to the aqueous humor of the eye. According to the '743 patent, the measurement of optical absorption is possible whereas measurement of the optical rotation through the aqueous humor is not possible. In the '743 patent, the intensity of the diffusely reflected light, however, may be analyzed to obtain useful information on the optical properties of the aqueous humor, including blood-glucose concentration.

U.S. Pat. No. 5,687,721 (the '721 patent), expressly incorporated by reference herein, also discloses a method of measuring blood-glucose concentration by generating both a measurement and reference polarized light beam, and comparing said beams to determine the angle of rotation, which is attributable to the blood-glucose concentration. The preferable testing site disclosed, however, is the finger or other suitable appendage according to the '721 patent. The '721 patent further discloses and requires the use of a monochromatic laser and/or semi-conductor as a light source.

U.S. Pat. No. 5,788,632 (the '632 patent), expressly incorporated by reference herein, discloses a non-invasive instrument for determining blood-glucose concentration by transmitting a first beam of light through a first polarizer and a first retarder, then directing the light through the sample to be measured, transmitting the light through a second polarizer or retarder, and lastly detecting the light from the second detector. The rotation of measured polarized light is correlated to the blood-glucose concentration of the sample measured according to the '632 patent.

U.S. Pat. No. 5,433,197 (the '197 patent), expressly incorporated by reference herein, discloses a non-invasive instrument for determining blood-glucose concentration using a broad-band of near-infrared radiation which illuminates the eye in such a manner that the energy passes through the aqueous humor in the anterior chamber of the eye and is then reflected from the iris. The reflected energy then passes back through the aqueous humor and the cornea and is collected for spectral analysis. According to the '197 patent, the electrical signals representative of the reflected energy are analyzed by univariate and/or multivariate signal processing techniques to correct for any errors in the glucose determination. Again, the accuracy of the instrument in the '197 patent is limited because glucose simply lacks a sufficiently distinguishable "fingerprint" in this near-infrared radiation spectrum.

Instruments and methods of using the body's naturally emitted radiation to measure blood-glucose concentration using the human-body, and in particular, the tympanic membrane as a testing site have also been disclosed. U.S. Pat. Nos. 4,790,324; 4,797,840; 4,932,789; 5,024,533; 5,167,235; 5,169,235; and 5,178,464, expressly incorporated by reference herein, describe various designs, stabilization techniques and calibration techniques for tympanic non-contact thermometers. In addition, U.S. Pat. No. 5,666,956 (the '956 patent), expressly incorporated by reference herein, discloses an instrument which measures electromagnetic radiation from the tympanic membrane and computes monochromatic emissivity using Plank's law by measuring the radiation intensity, spectral distribution, and blackbody temperature. According to the '956 patent, the resultant monochromatic emissivity is variable depending on the spectral characteristics of the site measured, namely the blood-glucose concentration measured from the tympanic membrane. It should be noted, however, that the '956 patent equates skin surfaces of the body to a "gray-body" rather than a black-body with respect to its monochromatic emissivity. Therefore, according to the '956 patent, the accuracy of such skin surface-based methods utilizing natural blackbody emitted radiation is not useful for analyte measurements, as compared to a method of subsurface analysis utilizing natural black-body radiation emitted from the tympanic membrane.

The human body naturally emits from its surfaces infrared radiation whose spectrum, or radiation signature, is modified by the presence, absence or concentration of analytes in the body tissues. The eye is particularly well suited as a testing site to detect this infrared radiation. For example, certain analytes, such as glucose, exhibit a minimal time delay in glucose concentration changes between the eye and the blood, and the eye provides a body surface with few interferences. Cameron et al., (3)2 DIABETES TECHNOL. THER., 202–207 (2001). There is, therefore, in the field of non-invasive blood analyte monitoring, an unmet need for a suitable instrument, and methodologies for using it, to accurately measure analyte concentrations, such as blood glucose concentration, as well as concentrations of other desired analytes, in subjects requiring this type of blood analyte measurement.

SUMMARY OF THE INVENTION

The present invention is related to non-invasive methods for measuring the presence or the concentration of a blood or tissue analyte, and instruments for making such measurements, utilizing the radiation signature of the natural blackbody radiation emission from a subject's body surface. The instruments and methods of the present invention do not require direct contact of the instrument with a surface of a subject's body in order to make the analyte measurements.

The analyte that is actually measured or detected may be any compound or substance that has a radiation signature in the mid-infrared range. In addition to directly measuring the presence, absence or concentration of a particular analyte, the methods and instrument of the present invention may also be used to detect the presence, absence or concentration of any compound or substance that represents a surrogate marker for or has a correlation to the presence, absence, or concentration of another analyte of interest, including but not limited to any metabolite or degradation product of an analyte, or an upstream or downstream pathway component or product that is affected by an analyte of interest. In this situation the analyte that is actually measured is a surrogate marker for another analyte of interest.

One embodiment of the present invention relates to a method of measuring an analyte concentration in the blood or tissue of a subject which may comprise detecting the level of mid-infrared radiation naturally emitted from a body surface of the subject, and determining the analyte concentration by correlating the spectral characteristics of the mid-infrared radiation to the analyte concentration, and analyzing this detected mid-infrared radiation to calculate the analyte concentration. In this embodiment, the detecting and correlating steps may further comprise using a microprocessor. The subject being tested may be any mammal or non-mammalian animal, and preferably the subject may be a human. Further, the analyte being measured may be a wide variety of analytes, including, but not limited to, analytes found in the blood or other tissues of a subject, airborne analytes such as those present in air that was contacted with or exhaled by a subject, metabolic compounds or substances, carbohydrates such as sugars including glucose, proteins, peptides, or amino acids, fats or fatty acids, triglycerides, polysaccharides, alcohols including ethanol, pharmaceutical or non-pharmaceutical compounds, substances, or drugs. In one embodiment, the analyte being measured is glucose. In addition, the body surface from which the radiation signature is obtained to determine the presence, absence or concentration of an analyte may be a wide variety of body surfaces, including, but not limited to, skin, the eye, mouth, nose, ear or any other orifices, cavities, piercing tracts or other surface of a subject's body whether naturally occurring or artificial such as a surgically created body surface.

In another embodiment, the present invention relates to an instrument which measures the level of mid-infrared radiation from a surface of a subject's body and determines a specific analyte's concentration based on the analyte's distinctive mid-infrared radiation signature. In another embodiment, the instrument may also comprise a microprocessor and a display. In another embodiment, the instrument may also comprise a wavelength selector which may further comprise a filter of any suitable type, including but not limited to, an absorption filter, interference filter, monochromator, linear variable filter, circular variable filter, and a prism. In another embodiment, the instrument may also comprise a mid-infrared light detector, which may be any suitable type, including, but not limited to a thermocouple, a thermistor, a microbolometer, and a liquid nitrogen cooled MTC.

In another embodiment of the present invention, the instrument may comprise a display, such as an alphanumeric display, including, but not limited to, a liquid crystal display (LCD), a plasma display panel (PDP), and a field emission display (FED). In another embodiment of the present invention, the instrument comprises an audio display which may be provided with an audio source comprising recorded audio clips, speech synthesizers and voice emulation algorithms to audibly report the analyte concentration.

In another embodiment, the instrument of the present invention comprises a microprocessor and a memory which is operatively linked to the microprocessor. The instrument of this embodiment may also further comprise a communications interface adapted to transmit data from the instrument to a computer system. In this embodiment, the communications interface selected may be any suitable interface, including, but not limited to, a serial, parallel, universal serial bus (USB), FireWire, Ethernet, fiber optic, co-axial, and twisted pair cables.

In another embodiment, the present invention relates to a computer system for downloading and storing measured analyte concentrations. This embodiment may further comprise a computer processor, a memory which is operatively linked to the computer processor, a communications interface adapted to receive and send data within the computer processor, and a computer program stored in the memory which executes in the computer processor. The computer processor of this embodiment further comprises a database, wherein data received by the processor may be stored on the memory as a database, and sorted into predetermined fields, and the database may be capable of graphical representations of the downloaded analyte concentrations. The graphical representations of this embodiment may include, but are not limited to, column, line, bar, pie, XY scatter, area, radar, and surface representations.

In another embodiment, the present invention relates to a computer interface which is further adapted to transmit data for analyte concentrations to a remote computer processor or user. In this embodiment, a remote user may be physicians, research institutes, specialists, nurses, hospice service providers, insurance carriers, and health care providers.

In a further embodiment, the present invention relates to a method or system for downloading and storing a subject's analyte concentrations which may comprise measuring the analyte concentration using a non-invasive instrument having a communications interface, connecting the non-invasive instrument through the communications interface to a computer system having a computer processor, a computer program which executes in the computer processor, and an analogous communications interface, and downloading the measured analyte concentrations from the non-invasive instrument to the computer system. The communications interface of this embodiment further comprises a communications interface adapted to transmit data from the instrument to a computer system. In this embodiment, the communications interface may include, for example, serial, parallel, universal serial bus (USB), FireWire, Ethernet, fiber optic, co-axial, and twisted pair cables.

Other objectives, features and advantages of the present invention will become apparent from the following detailed description. The detailed description and the specific examples, although indicating specific embodiments of the invention, are provided by way of illustration only. Accordingly, the present invention also includes those various changes and modifications within the spirit and scope of the invention that may become apparent to those skilled in the art from this detailed description.

DETAILED DESCRIPTION OF THE INVENTION

Figure 1:
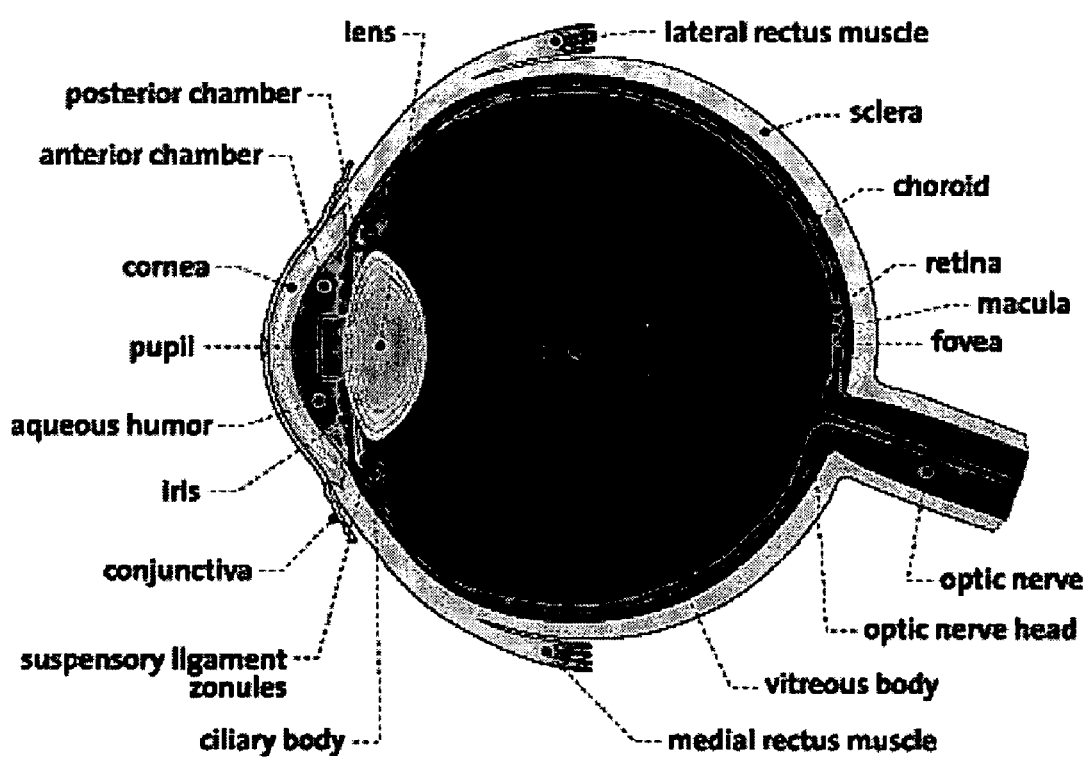
FIG. 1: Provides a graphical illustration of the human eye.
Figure 2:
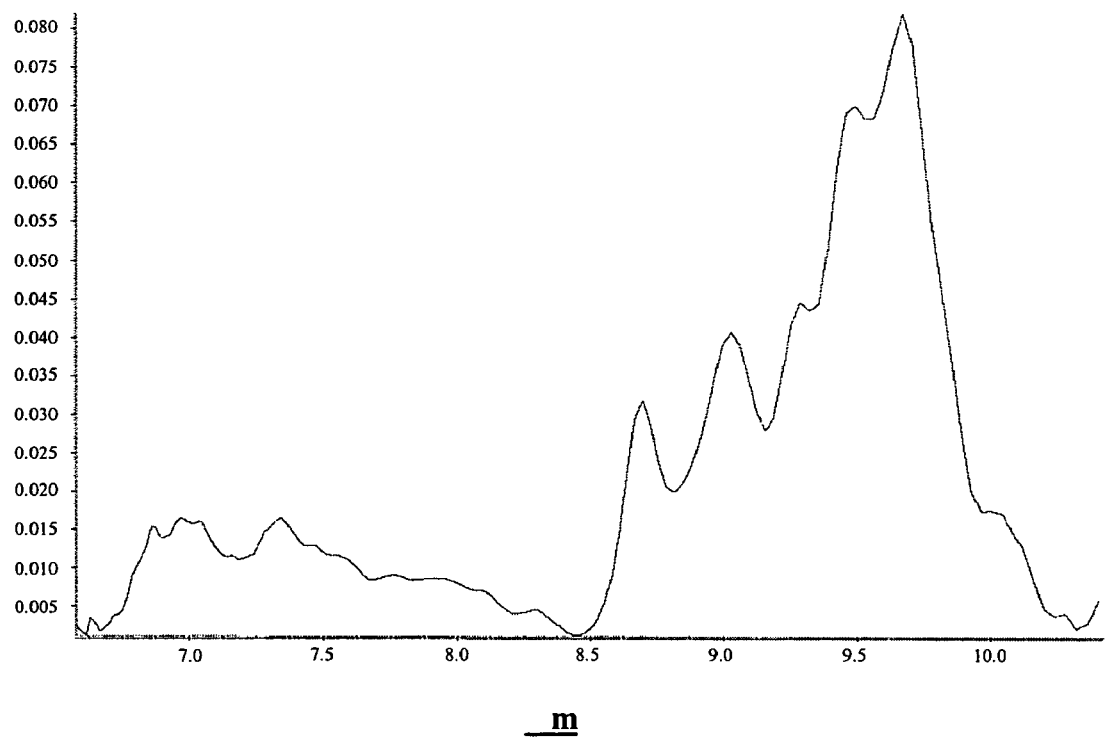
FIG. 2: Provides a chart that depicts the mid-infrared radiation spectral fingerprint for glucose.

It is understood that the present invention is not limited to the particular methodologies, protocols, instruments, and systems, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise. Thus, for example, a reference to "a mid-infrared filter" is a reference to one or more filters and includes equivalents thereof known to those skilled in the art, and so forth.

Unless defined otherwise, all technical and scientific terms used herein have the same meanings as commonly understood by one of ordinary skill in the art to which this invention belongs. Preferred methods, devices, and materials are described, although any methods and materials similar or equivalent to those described herein can be used in the practice or testing of the present invention. All references cited herein are incorporated by reference herein in their entirety.

DEFINITIONS

Analyte: As used herein describes any particular substance to be measured. Analyte may also include any substance in the tissue of a subject, or is present in air that was in contact with or exhaled by a subject, which demonstrates and infrared radiation signature. Examples of analytes include, but are not limited to, metabolic compounds or substances, carbohydrates such as sugars including glucose, proteins, peptides, or amino acids, fats or fatty acids, triglycerides, polysaccharides, alcohols including ethanol, toxins, hormones, vitamins, bacteria-related substances, fungus-related substances, virus-related substances, parasite-related substances, pharmaceutical or non-pharmaceutical compounds, substances, pro-drugs or drugs, and any precursor, metabolite, degradation product or surrogate marker of any of the foregoing. Analyte may also include any substance which is foreign to or not normally present in the body of the subject.

Far-Infrared Radiation: As used herein refers to any radiation, either generated from any source or naturally emitted, having wavelengths of about 50.00 to about 1000.00 microns.

Focused: As used herein means mostly parallel rays of light that are caused to converge on a specific predetermined point.

Infrared Radiation: As used herein refers to any radiation, either generated from any source or naturally emitted, having wavelengths of about 0.78 to about 1000.00 microns.

Mid-Infrared Radiation: As used herein refers to any radiation, either generated from any source or naturally emitted, having wavelengths of about 2.50 microns to about 50.00 microns.

Mid-Infrared Radiation Detector: As used herein refers to any detector or sensor capable of registering infrared radiation. Examples of a suitable infrared radiation detectors, include but are not limited to, a thermocouple, a thermistor, a microbolometer, and a liquid nitrogen cooled MTC. The combined detected infrared radiation may be correlated with wavelengths corresponding to analyte concentrations using means such as the Fourier transform to produce high resolution spectra.

Near-Infrared Radiation: As used herein refers to any radiation, either generated or naturally emitted, having wavelengths of about 0.78 to about 2.50 microns.

Surface: As used herein refers to any part of a subject's body that may be exposed to the external environment, including but not limited to, skin, the eye, ear, mouth, nose or any other orifice, body cavities, piercing tracts or other surface whether naturally occurring or artificial such as a surgically created surface.

Tissue: As used herein includes any tissue or component of a subject, including, but not limited to, skin, blood, body fluids, the eye, interstitial fluid, ocular fluid, bone, muscle, epithelium, fat, hair, fascia, organs, cartilage, tendons, ligaments, and any mucous membrane.

Non-invasive Glucose Measurement

Figure 3:
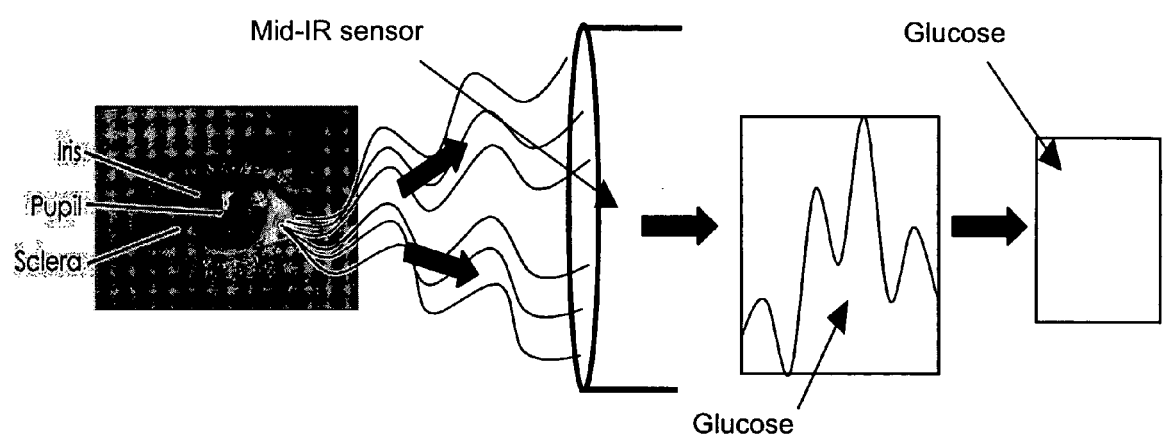
FIG. 3: Provides a graphical illustration of one embodiment of the present invention, wherein analyte concentration is measured from the mid-infrared radiation reflected back from the eye.

Human beings are natural emitters or radiators of energy in the mid-infrared radiation spectrum. In one aspect of the present invention, the body acts as its own light (or heat) source, providing the mid-infrared radiation signature of the analytes present therein. In this aspect, and with respect to the surfaces of a subject's body, light (or heat) from the body is emitted or radiated from a body surface, and is detected by a mid-infrared detection instrument. The mid-infrared radiation signature in the body's mid-infrared radiation emission is affected by the presence, absence or concentration of analytes, such as glucose, in the tissues of a subject. The natural mid-infrared radiation signature of glucose contained within the body's natural mid-infrared radiation signature provides the basis for a non-invasive glucose measurement method and instruments for making such measurements (FIG. 3). In addition, decreasing or increasing the concentration of certain analytes may cause an increase in the body's natural emission of infrared radiation. Such an increase in the body's natural infrared radiation emission may provide a measurable signal that may be utilized to measure the presence, absence or concentration of an analyte.

There is substantial evidence that fluctuations in blood glucose levels are well correlated with glucose levels in the aqueous humor of the eye. (Steffes, 1(2) DIABETES TECHNOL. THER., 129–133 (1999)). In fact, it is estimated that the time delay between the blood and aqueous humor glucose concentration averages only about five minutes. (Cameron et al., 3(2) DIABETES TECHNOL. THER., 201–207 (2001)). The aqueous humor is a watery liquid that lies between the lens and cornea, which bathes and supplies the nutrients to the cornea, lens and iris (FIG. 1). The glucose in the eye is located throughout the various components and compartments of the eye, including, but not limited to, epithelial cells, the aqueous humor, the vitreous humor, various layers of the cornea, iris, various layers of the sclera, conjunctiva, tears, and blood vessels. Therefore, the eye is both an ideal and suitable body surface for non-invasive measurement of the presence, absence or concentration of analytes in the tissue of a subject.

Measuring Mid-infrared Radiation

When electromagnetic radiation is passed through a substance, it can either be absorbed or transmitted, depending upon its frequency and the structure of the molecules it encounters. Electromagnetic radiation is energy and hence when a molecule absorbs radiation it gains energy as it undergoes a quantum transition from one energy state ($E_{initial}$) to another ($E_{final}$). The frequency of the absorbed radiation is related to the energy of the transition by Planck's law: $E_{final}-E_{initial}=E=hn=hc/l$. Thus, if a transition exists which is related to the frequency of the incident radiation by Planck's constant, then the radiation can be absorbed. Conversely, if the frequency does not satisfy the Planck expression, then the radiation will be transmitted. A plot of the frequency of the incident radiation vs. some measure of the percent radiation absorbed by the sample is the radiation signature of the compound. The absorption of some amount of the radiation that is applied to a substance, or body surface containing substances, that absorbs radiation may result in a measurable decrease in the amount of radiation energy that actually passes through, or is affected by, the radiation absorbing substances. Such a decrease in the amount of radiation that passes through, or is affected by, the radiation absorbing substances may provide a measurable signal that may be utilized to measure the presence, absence or the concentration of an analyte.

The human body emits electromagnetic radiation within the infrared radiation spectrum. The spectral characteristics of the infrared radiation emitted can be correlated with the properties of the emitting object, such as a subject's body surface. For example, glucose absorbs mid-infrared radiation at wavelengths between about 8.0 microns to about 11.0 microns. If mid-infrared radiation passes through or reflects from an object where glucose is present, a distinct radiation "fingerprint" or "signature" can be detected from the remaining light that is not absorbed, creating a radiation signature. The radiation signature created can both confirm the presence or absence of an analyte and indicate the concentration of an analyte. In addition, since glucose is a radiation absorbing substance, there may be a measurable decrease in the amount of radiation energy that passes through or reflects from a glucose containing material such as the body surfaces of a subject, including the subject's eye. This measurable decrease in the amount of radiation energy may be utilized to measure the presence, absence or concentration of glucose in a subject.

One embodiment of the present invention provides a method for non-invasively measuring the analyte concentration in a tissue of a subject, such as blood, comprising the steps of detecting mid-infrared radiation emitted by the subject, and determining the concentration of said analyte by correlating the spectral characteristics of the detected mid-infrared radiation with a radiation signature that corresponds to the analyte concentration, and analyzing the radiation signature to give an accurate analyte concentration measurement. In another embodiment, the method includes a filtering step before detection by filtering the naturally emitted infrared radiation from the body surface so that only wavelengths of about 8.00 microns to about 11.00 pass through the filter. In this embodiment, the filtering step may be accomplished using absorption filters, interference filters, monochromators, linear and circular variable filters, prisms or any other functional equivalent known in the art. The detecting step may be accomplished using any mid-infrared radiation sensor known in the art, including, but not limited to a thermocouple, thermistor, microbolometer, a liquid nitrogen cooled MTC, or any other functional equivalent known in the art. Correlating the spectral characteristics of the detected mid-infrared radiation may comprise the use of a microprocessor to correlate the detected mid-infrared radiation signature with a radiation signature of an analyte. If the analyte being measured is glucose, then the generated radiation signature may be within the wavelength range within about 8.0 to about 11.0 microns. The analyzing step may further comprise a microprocessor using algorithms based on Plank's law to correlate the radiation signature with glucose concentration.

In another embodiment of the present invention, an instrument comprising a mid-infrared radiation detector and a display may be held up to a body surface of a subject. The naturally emitted infrared radiation from the body surface may optionally be filtered so that only wavelengths of about 8.0 microns to about 11.0 microns reach the mid-infrared radiation detector, if glucose is the analyte of interest. The radiation signature of the mid-infrared radiation detected by the detector may then be correlated with a radiation signature that corresponds to a glucose concentration. The radiation signature may then be analyzed to give an accurate glucose concentration measurement. The measured glucose concentration may be displayed.

The instrument of the present invention may also comprise a mid-infrared radiation detector for detecting mid-infrared radiation. The mid-infrared radiation detector can measure the naturally emitted mid-infrared radiation in any form, including in the form of heat energy. Detecting the naturally emitted mid-infrared radiation may be accomplished using thermocouples, thermistors, microbolometers, liquid nitrogen cooled MTC, or any other functional equivalent known in the art. Both thermocouples and thermistors are well known in the art and are commercially available. For example, thermocouples are commonly used temperature sensors because they are relatively inexpensive, interchangeable, have standard connectors and can measure a wide range of temperatures (http://www.picotech.com). In addition, Thermometrics product portfolio comprises a wide range of thermistors (thermally sensitive resistors) which have, according to type, a negative (NTC), or positive (PTC) resistance/temperature coefficient (http://www.thermometrics.com).

The instrument of the present invention may also comprise a microprocessor. The microprocessor of this embodiment correlates the detected mid-infrared radiation with a radiation signature whose spectral characteristics provide information to the microprocessor about the analyte concentration being measured. The microprocessor of this embodiment analyzes the resultant radiation signature using algorithms based on Plank's law to translate the radiation signature into an accurate analyte concentration measurement in the sample being measured.

Clinical Applications

It may be required for diabetes patients and subjects at risk for diabetes to measure their blood glucose levels regularly in an attempt to keep their blood glucose levels within an acceptable range, and to make an accurate recordation of blood-glucose levels for both personal and medical records. In one aspect of the present invention, the instrument may also comprise an alphanumeric display for displaying the measured blood-glucose concentration. The alphanumeric display of this embodiment may comprise a visual display and an audio display. The visual display may be a liquid crystal display (LCD), a plasma display panel (PDP), and a field emission display (FED) or any other functional equivalent known in the art. An audio display, capable of transmitting alphanumeric data and converting this alphanumeric data to an audio display, may be provided with an audio source comprising recorded audio clips, speech synthesizers and voice emulation algorithms or any other functional equivalent known in the art.

Self-Monitoring of Blood Glucose (SMBG) is an ongoing process repeated multiple times per day for the rest of the diabetic patient's lifetime. Accurate recordation of these measurements are crucial for diagnostic purposes. A facile storage and access system for this data is also contemplated in this invention. In one aspect of the present invention, an instrument for non-invasively measuring blood-glucose concentration further comprises a microprocessor and a memory which is operatively linked to the microprocessor for storing the blood glucose measurements. The instrument of this embodiment further comprises a communications interface adapted to transmit data from the instrument to a computer system. In this embodiment the communications interface selected may include, for example, serial, parallel, universal serial bus (USB), FireWire, Ethernet, fiber optic, co-axial, and twisted pair cables or any other functional equivalent known in the art.

In addition to storing blood-glucose measurement data within an instrument, the present invention includes a computer system for downloading and storing these measurement data to facilitate storage and access to this information. The present invention further contemplates a computer processor, a memory which is operatively linked to the computer processor, a communications interface adapted to receive and send data within the computer processor, and a computer program stored in the memory which executes in the computer processor. The computer program of this embodiment further comprises a database, wherein data received by the database may be sorted into predetermined fields, and the database may be capable of graphical representations of the downloaded analyte concentrations. The graphical representations of this embodiment may include, but are not limited to, column, line, bar, pie, XY scatter, area, radar, and surface representations.

The computer system contemplated by the present invention should be accessible to a remote access user via an analogous communications interface for use as a diagnostic, research, or other medically related tool. Physicians, for example, could logon to the computer system via their analogous communications interface and upload a patient's blood-glucose measurements over any period of time. This information could provide a physician with an accurate record to use as a patient monitoring or diagnostic tool such as, for example, adjusting medication levels or recommending dietary changes. Other remote access users contemplated may include research institutes, clinical trial centers, specialists, nurses, hospice service providers, insurance carriers, and any other health care provider.

The present invention has demonstrated that glucose may be non-invasively measured using a mid-infrared signal from a body surface. Studies may be performed in a variety of systems, including studies with human corneas, in vitro studies using glucose solutions on membrane samples, rabbit studies with varying blood glucose concentrations, and human studies with diabetic or non-diabetic human volunteers.

The human studies will demonstrate a dose-response to glucose concentration.

EXAMPLES

The following examples are provided to describe and illustrate the present invention. As such, they should not be construed to limit the scope of the invention. Those in the art will well appreciate that many other embodiments also fall within the scope of the invention, as it is described hereinabove and in the claims.

Example 1

Experimental In-Vitro Model to Test Precision and Accuracy of the Instrument Instrumentation An instrument used for the Mid-infrared measurements may be the SOC 400 portable FTIR. The SOC 400 portable FTIR is based on an interferometer and was originally designed for the US Army to detect battlefield gases. This instrument may be modified to allow measurements on rabbit and human eyes. These modifications may include the installation of a filter to allow only energy in a desired wavelength region, such as between 7 to 13 micron region, to be measured, and also the modification of the faceplate to permit easier placement of the instrument for rabbit and human studies.

In Vitro Studies

Studies are performed to demonstrate that solutions with varying concentrations of glucose would give a Mid-infrared dose-response. Hydrophilic polyethylene membranes from Millipore Corporation are saturated with glucose solutions with concentrations at 2000 mg/dL and lower. The samples are warmed to approximately body temperature before measurements are taken, which simulates the natural mid-infrared radiation from a subject's body.

Example 2

Experimental Rabbit Model

An initial test is conducted using two adult rabbits having glucose values below 150 mg/dL. The rabbits are anesthetized with an IM injection of ketamine/xylazine/acepromazine according to the protocol described in Cameron, et al., 1(2) DIABETES TECH. THER., 135–143 (1999). The rabbit is immobilized such that after anesthesia the eyeball is available for measurements with the non-invasive glucose monitor as contemplated in the present invention.

Once the animals are unconscious, a drop of blood from the ear vein of each is taken and tested on a blood glucose test strip with a blood glucose meter. Such samples are taken every fifteen minutes throughout the study.

Each rabbit is placed in front of, or under, a non-invasive glucose monitor as contemplated in the present invention, or such instrument is brought up to a body surface of the rabbit, and a series of measurements are taken over the next several hours. One rabbit is tested by simply measuring the infrared radiation naturally emitted from the rabbit's eye. The second rabbit will be tested by flooding infrared radiation onto the rabbit's eye and measuring the reflected signal. Every fifteen minutes a blood glucose test is performed using a drop of blood from each rabbit for comparison with the data generated using the non-invasive glucose monitor of the present invention. The data generated in this study is used to show that the instrument according to the present invention is measuring blood glucose concentration.

Ketamine Anesthetized Rabbit Studies

As noted in the scientific literature (Cameron et al., DIABETES TECH. THER., (1999) 1(2):135–143), rabbits anesthetized with Ketamine experience a rapid and marked increase in blood glucose concentration, due to the release of glucose from the liver. Rabbit blood sugar can change from ~125 mg/dL to ~325 mg/dL in 60 minutes, as measured with a LXN ExpressView blood glucose meter. These experiments require a preliminary use of gas anesthesia (Isoflorane) prior to the use of Ketamine. The gas must be discontinued in order for the Ketamine effect to manifest itself. The drying out of the eye may be prevented by suturing the eyelids and using the sutures to open the eye for the measurement and then allowing them to close after the measurement to moisten the eyeball. Once the rabbit is treated with the ketamine, measurements are taken from the eye of the rabbit to measure its natural mid-infrared radiation and glucose concentration.

Example 3

Human Clinical Study

Human Studies

Several studies may be performed with non-diabetic and diabetic human volunteers. Several experiments with a diabetic volunteer may be performed. The subject is asked to adjust his food intake and insulin administration in order to have his glucose levels move from approximately 100 to 300 mg/dL over a three to four hour timeframe. During the study, the patient takes duplicate fingerstick glucose measurements every ten to fifteen minutes and is scanned with the SOC 400 approximately every fifteen minutes. Prior to collecting the infrared scan, the instrument operator aligns the SOC 400 with the subjects' eye to attempt to collect the strongest signal. Measurements of the mid-infrared radiation emitted from the subject's eye are taken and glucose concentration is measured.

Example 4

Figure 4:
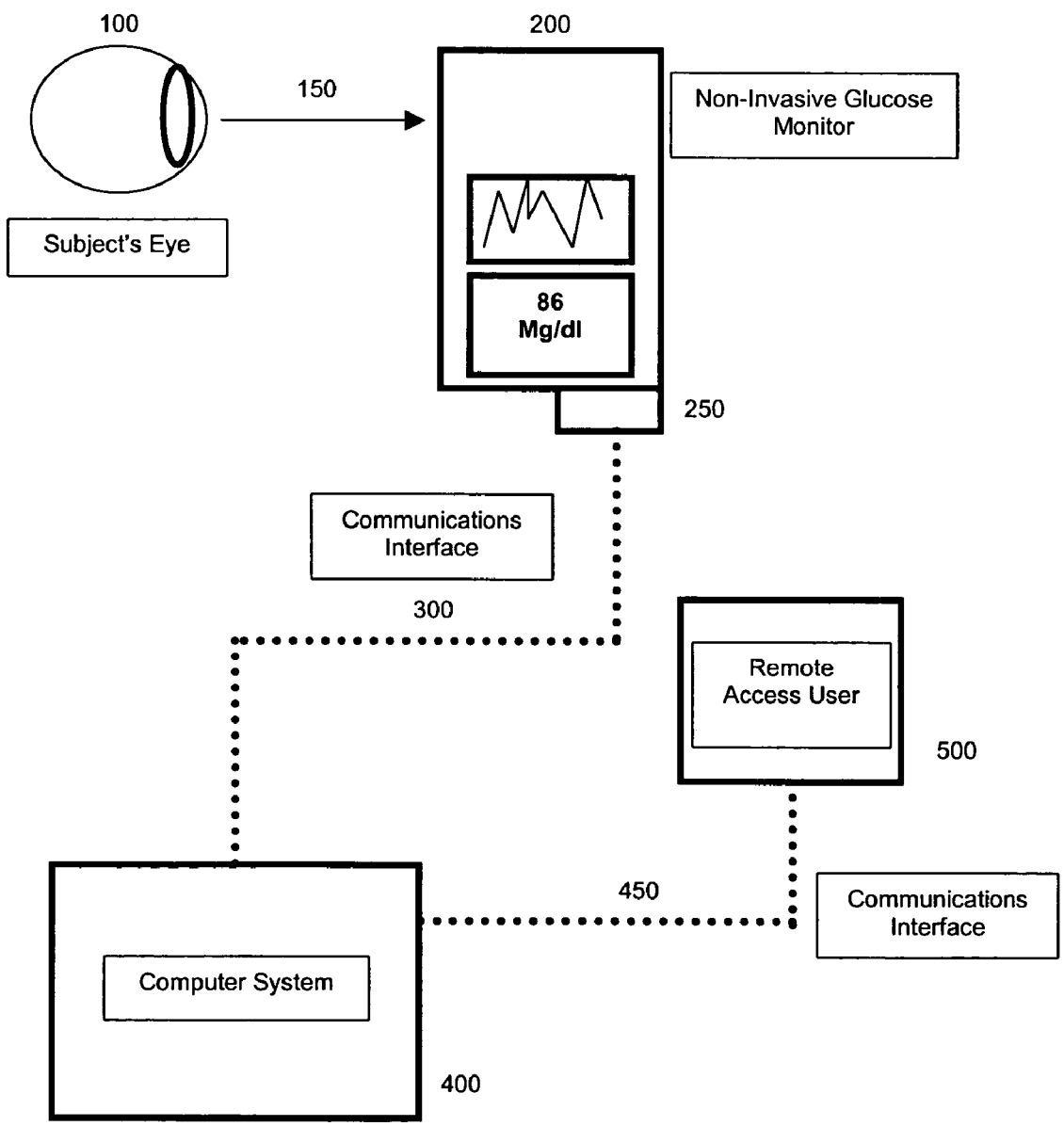
FIG. 4: Provides a flowchart of one embodiment of the present invention, comprising a method wherein a remote access user can receive a subject's measured analyte concentrations which have been downloaded and stored in a computer system.

A Method Wherein a Remote Access User Can Receive a Subject's Measured Analyte Concentrations Which Have Been Downloaded and Stored in a Computer System One aspect of the present invention relates to a method of downloading and storing a subject's measured analyte concentrations (FIG. 4). A subject first measures the analyte concentration from a body surface such as their eye (100), whereby naturally emitted mid-infrared radiation (150) is measured using a non-invasive instrument (200). The non-invasive instrument (200) further comprises a communications interface (250) which is capable of connecting (300) the non-invasive instrument (200) through the communications interface (250) to a computer system (400). The communications interface (250) is specifically adapted to transmit data from the instrument to the computer system (400). The computer system (400) comprises a computer processor, a computer program which executes in the computer processor, and an analogous communications interface (450). The measured analyte concentrations from the non-invasive instrument (200) are downloaded via the communications interface (250) to the computer system (400). A remote access user (500), having a computer system with an analogous communications interface (450) is capable of retrieving the downloaded measured analyte concentrations from the computer system (400). The communications interfaces (250, 450) may include, for example, serial, parallel, universal serial bus (USB), FireWire, Ethernet, fiber optic, co-axial, and twisted pair cables. This information is used, for example, to provide data, warnings, advice or assistance to the patient or physician, and to track a patient's progress throughout the course of the disease.

What is claimed is:

1. A method of determining an analyte concentration in a tissue of a subject, the subject including an eye with an occular surface and a conjunctiva surface, comprising the steps:
   a. detecting naturally occurring mid-infrared radiation emitted from the conjunctiva without contact with the ocular surface using a non-invasive instrument comprising a mid-infrared detector;
   b. comparing a radiation signature of said mid-infrared radiation to a radiation signature of mid-infrared radiation corresponding to an analyte concentration; and
   c. analyzing said radiation signature of said mid-infrared radiation from said subject to determine said analyte concentration in a tissue of said subject.

2. The method of claim 1, wherein said analyte is selected from the group consisting of metabolic compounds or substances, carbohydrates, sugars, glucose, proteins, peptides, amino acids, fats, fatty acids, triglycerides, polysaccharides, alcohols, ethanol, toxins, hormones, vitamins, bacteria-related substances, fungus-related substances, parasite-related substances, pharmaceutical compounds, non-pharmaceutical compounds, pro-drugs, drugs, and any precursor, metabolite, degradation product or surrogate marker.

3. The method of claim 2, wherein said analyte is glucose.

4. The method of claim 1, wherein said naturally occurring mid-infrared radiation comprises infrared radiation having wavelengths between about 2.5 microns and about 25.0 microns.

5. The method of claim 1, wherein said detecting step further comprises selecting and detecting desired wavelengths of said naturally occurring mid-infrared radiation.

6. The method of claim 1, wherein said comparing step and said analyzing step further comprise using a microprocessor.

7. A method of downloading and storing a subject's measured analyte concentration, comprising the steps of: a. measuring said analyte concentration according to the method of claim 1, using a non-invasive mid-infrared detecting instrument having a communications interface; b. connecting said instrument through said communications interface to a computer system having a computer processor, a computer program which executes in said computer processor, and an analogous communications interface; and c. downloading from said instrument to said computer system said measured analyte concentrations.

* * * * *

(12) EX PARTE REEXAMINATION CERTIFICATE (6125th)
United States Patent
Burd et al.

(10) Number: US 6,958,039 C1
(45) Certificate Issued: Feb. 19, 2008

(54) METHOD AND INSTRUMENTS FOR NON-INVASIVE ANALYTE MEASUREMENT

(75) Inventors: John F. Burd, San Diego, CA (US); Gary Krantz, Laguna Beach, CA (US); William Sell, Petaluma, CA (US)

(73) Assignee: Oculir, Inc., San Diego, CA (US)

Reexamination Request:
No. 90/008,214, Sep. 14, 2006

Reexamination Certificate for:
Patent No.: 6,958,039
Issued: Oct. 25, 2005
Appl. No.: 10/824,254
Filed: Apr. 14, 2004

Related U.S. Application Data
(60) Provisional application No. 60/467,355, filed on May 2, 2003.

(51) Int. Cl.
*A61B 5/00* (2006.01)

(52) U.S. Cl. .................. 600/309; 600/365; 600/473
(58) Field of Classification Search ................. None
See application file for complete search history.

(56) References Cited

U.S. PATENT DOCUMENTS

| 6,544,193 | B2 | 4/2003 | Abreu |
| 2002/0049389 | A1 | 4/2002 | Abreu |

OTHER PUBLICATIONS

The Photonics Design and Applications Handbook, The Photonic Spectrum Reference Chart, p. H–20, 44th International Edition, Laurin Publishing Co., Inc., 1998.

*Primary Examiner*—Beverly M. Flanagan

(57) ABSTRACT

The present invention is related to optical non-invasive methods and instruments to detect the level of analyte concentrations in the tissue of a subject. The spectra of mid-infared radiation emitted from a subject's body are altered corresponding to the concentration of various compounds within the radiating tissue. In one aspect of the invention, an instrument measures the level of mid-infrared radiation from the subject's body surface, such as the eye, and determines a specific analyte's concentration based on said analyte's distinctive mid-infrared radiation signature.

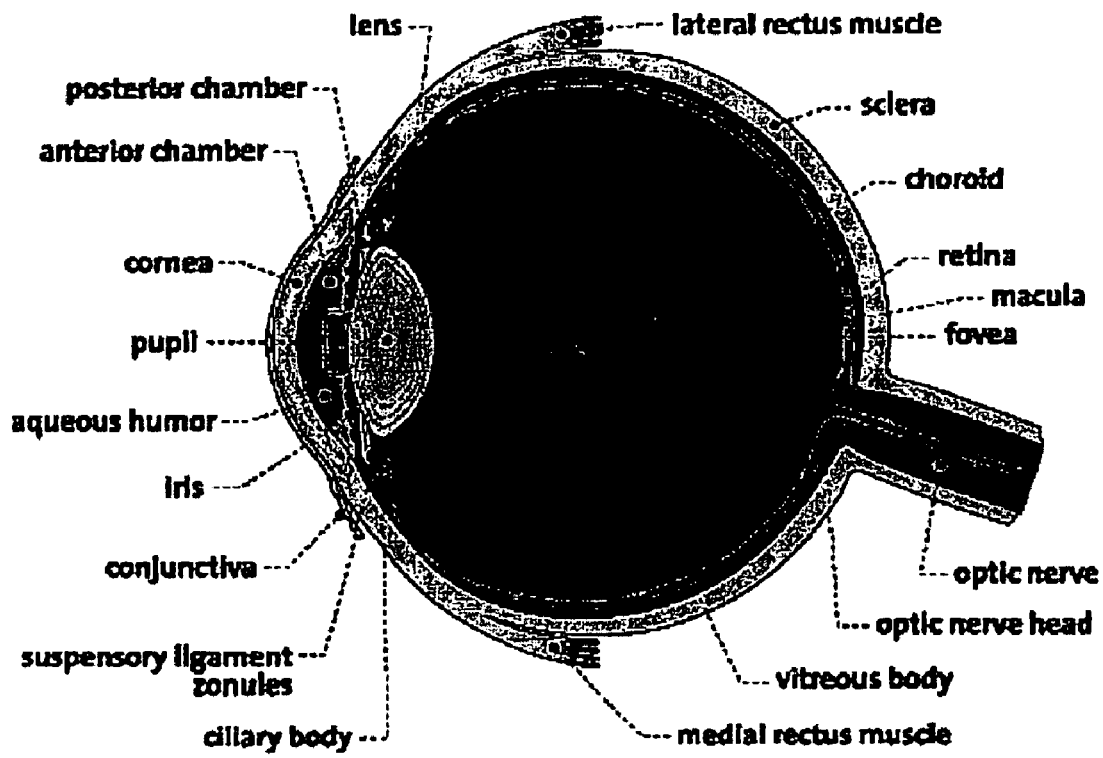

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–7 are cancelled.

* * * * *